United States Patent [19]

Decker et al.

[11] 4,414,411

[45] Nov. 8, 1983

[54] PROCESS FOR PREPARING UNSATURATED ACIDS WITH MO, V, TI-CONTAINING CATALYSTS

[75] Inventors: Harry J. Decker; Erlind M. Thorsteinson, both of Charleston, W. Va.

[73] Assignee: Union Carbide Corporation, Danbury, Conn.

[21] Appl. No.: 146,655

[22] Filed: May 5, 1980

Related U.S. Application Data

[63] Continuation-in-part of Ser. No. 408,416, Oct. 23, 1973, abandoned.

[51] Int. Cl.$^3$ .................... C07C 51/25; C07C 57/055
[52] U.S. Cl. .................... 562/534; 260/413; 562/535; 562/546; 562/547; 502/241; 502/242; 502/309
[58] Field of Search ............... 562/535, 534; 260/413; 252/469, 464, 455 R, 456

[56] References Cited

U.S. PATENT DOCUMENTS

| | | | |
|---|---|---|---|
| 3,236,782 | 2/1966 | Koch | 562/535 |
| 3,541,143 | 11/1970 | Nakano et al. | 562/535 |
| 3,567,772 | 3/1971 | Yanagita et al. | 562/535 |
| 3,574,729 | 4/1971 | Gasson | 562/535 |
| 3,702,868 | 11/1972 | Santangelo | 562/532 |
| 3,773,692 | 11/1973 | Hensil et al. | 562/535 |
| 4,014,927 | 3/1977 | Kadowaki | 562/534 |

*Primary Examiner*—Vivian Garner
*Attorney, Agent, or Firm*—Bernard Francis Crowe

[57] ABSTRACT

A novel catalyst comprising the elements Mo, V and Ti, and an oxidation process, is provided for oxidizing alpha beta unsaturated aliphatic aldehydes in the vapor phase with molecular oxygen to produce the corresponding alpha-beta unsaturated carboxylic acid.

20 Claims, No Drawings

PROCESS FOR PREPARING UNSATURATED ACIDS WITH MO, V, TI-CONTAINING CATALYSTS

This is a continuation-in-part of Ser. No. 408,416 filed Oct. 23, 1973, abandoned.

BACKGROUND OF THE INVENTION

1. Field of the Invention

The invention relates to the vapor phase catalytic oxidation of unsaturated aliphatic aldehydes to the corresponding unsaturated aliphatic carboxylic acid.

2. Description of the Prior Art

The use of molybdenum and vanadium containing catalyst systems for the gas phase oxidation of alpha-beta unsaturated aliphatic aldehydes, such as acrolein, to the corresponding alpha-beta-unsaturated carboxylic acids, such as acrylic acid, has been known.

In these reactions a gaseous reaction mixture which usually contains the aldehyde, molecular oxygen and water, as steam, is brought into contact with the catalyst, by continuously passing a stream of the reaction mixture through a bed of the catalyst. Such known catalyst systems would include those disclosed in the following U.S. Pat. Nos.: 3,087,964; 3,358,020; 3,408,392; 3,435,069; 3,439,028; 3,530,175; 3,567,772; 3,567,773; 3,574,729; 3,644,509; 3,655,749; 3,670,017 and 3,703,548. Not all of these catalyst systems, however, are currently useful for commercial purposes. Some of these catalyst systems, for example, do not provide the relatively high levels of % conversion, productivity and % selectivity, which are all required, presently, of a commercially useful catalyst system.

The terms % conversion, productivity, and % selectivity which are employed herein with respect to the present invention are defined as follows:

$$\% \text{ conversion} = 100 \times \frac{A}{\text{moles of aldehyde in the reaction mixture which is fed to the catalyst bed per hour of reaction time}} \quad \text{I}$$

wherein $A$ = the molar aldehyde-equivalent sum (carbon basis) of all carbon-containing products, excluding the aldehyde in the effluent, which are produced per hour of reaction time  Ia productivity = pounds of alpha-beta unsaturated aliphatic carboxylic acid product produced per cubic foot of catalyst (in the catalyst bed) per hour of reaction time  II $$\% \text{ selectivity} = 100 \times \frac{\text{moles of alpha-beta-unsaturated aliphatic carboxylic acid produced per hour of reaction time}}{A} \quad \text{III}$$

wherein A is as defined above in equation Ia.

SUMMARY OF THE INVENTION

Alpha-beta-unsaturated aliphatic carboxylic acids are produced with a relatively high % conversion, productivity and % selectivity by oxidizing the corresponding alpha-beta-unsaturated aldehyde in the vapor phase by contacting the aldehyde, in the presence of molecular oxygen and steam, with certain catalyst compositions containing molybdenum, vanadium and titanium.

An object of the present invention is to provide novel catalyst compositions for the vapor phase oxidation of alpha-beta-unsaturated aliphatic aldehydes to the corresponding alpha-beta-unsaturated aliphatic carboxylic acid.

A further object of the present invention is to provide a process whereby alpha-beta-unsaturated aliphatic aldehydes can be oxidized in the gas phase so to produce the corresponding alpha-beta unsaturated aliphatic carboxylic acid with a relatively high level of % conversion, productivity and % selectivity.

These and other objects of the present invention are achieved by using as such a catalyst in such a process a composition comprising the elements Mo, V, Ti and X in the ratio

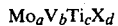

$$Mo_a V_b Ti_c X_d$$

wherein X is Fe, Cu, Co, Cr, and/or Mn
a is 12,
b is 1 to 14, and preferably 2 to 8,
c is 0.1 to 12, and preferably 0.5 to 2, and
d is 0 to 3.0, and preferably 0.01 to 1.0.

The numerical values of a, b, c and d represent the relative atom-mole ratios of the elements Mo, V, Ti, and X, respectively, which are present in the catalyst composition.

THE CATALYST

The elements Mo, V, Ti, and X present in the catalyst composition in combination with oxygen in the form, it is believed, of various metal oxides.

The catalyst is preferably prepared from a solution of soluble salts and/or complexes and/or compounds of each of the metals Mo, V, Ti and X. The solution is preferably an aqueous system having a pH of 1–12, and preferably 5±3, at a temperature of about 20° to 100° C. The solution of the metal containing compounds is prepared by dissolving sufficient quantities of soluble compounds of each of the metals, so as to provide the desired a:b:c:d atom-mole ratios of the elements Mo, V, Ti and X, respectively. The selected salts, complexes or compounds of the metals Mo, V and Ti should be mutually soluble. If the selected salts, complexes or compounds of the metal X are not mutually soluble with the other compounds, they can be added last to the solution system. The catalyst composition is then prepared by removing the water or other solvent from the mixture of the metal compounds in the solution system. Any portion, and preferably i.e. about <50 weight %, of the titanium may be replaced by tantalum and/or niobium in the catalyst composition.

The water or other solvent can be removed from the mixture of the dissolved metal compounds by evaporation.

Where the catalyst is to be used on a support, the metal compounds are deposited on a porous support usually having a surface area of about 0.01 to 2 square meters per gram. The support has an apparent porosity of 30–60%; at least 90% of the pores have a pore diameter in the range of 20–1500 microns. The support is usually used in the form of particles or pellets which are about ⅛ to 5/16 inch in diameter. The deposition is accomplished by immersing the support in the solution and then evaporating off the major portion of the solvent, and then drying the system at about 80° to 140° C. for 2 to 60 hours. The dried catalyst is then calcined by being heated at 250° to 450° C., and preferably 325°–425° C., for 2 to 24 hours in air to produce the desired $$Mo_aV_bTi_cX_d$$

composition.

When used on the support, the supported oxides usually comprise about 10 to 50 weight % of the total catalyst composition; of the total catalyst composition about 50 to 90 weight % is support.

The molybdenum is preferably introduced into solution in the form of ammonium salts thereof such as ammonium paramolybdate, and organic acid salts of molybdenum such as acetates, oxalates, mandelates and glycolates. Other water soluble molybdenum compounds which may be used are partially water soluble molybdenum oxides, molybdic acid, and the nitrates and chlorides of molybdenum.

The vanadium is preferably introduced into solution in the form of ammonium salts thereof such as ammonium meta-vanadate and ammonium decavanadate, and organic acid salts of vanadium such as acetates, oxalates and tartrates. Other water soluble vanadium compounds which may be used are partially water soluble vanadium oxides, and the sulfates and nitrates of vanadium.

The titanium is preferably introduced into solution in the form of a water soluble chelate coordinated with ammonium lactate. Other soluble titanium compounds which may be used are those in which titanium is coordinated, bonded, or complexed to a beta-diketonate, a carboxylic acid, an amine, an alcohol or an alkanolamine.

Where tantalum and/or niobium are used for a portion of the titanium, they are preferably introduced into solution in the form of oxalates. Other sources of soluble tantalum and niobium which may be used are tantalum and niobium compounds in which the tantalum or niobium is coordinated, bonded, or complexed to a beta-diketonate, a carboxylic acid, an amine, an alcohol or an alkanolamine.

The iron, copper, cobalt, chromium and manganese are preferably introduced into solution in the form of nitrates. Other water soluble compounds of these elements which may be used are the water soluble chlorides and organic acid salts such as the acetates, oxalates, tartrates, lactates, salicylates, formates and carbonates of such metals.

It is believed that, for the catalysts to be most effective, the Mo, V, Ti, X metal components should be reduced below their highest possible oxidation states. This may be accomplished during the thermal treatment of the catalyst in the presence of reducing agents such as $NH_3$ or organic reducing agents, such as the organic complexing agents, which are introduced into the solution systems from which the catalysts are prepared. The catalyst may also be reduced in the reactors in which the oxidation reaction is to be conducted by the passage of hydrocarbon reducing agents such as propylene through the catalyst bed.

THE ALDEHYDES

The alpha-beta-unsaturated aldehydes which are oxidized in the process of the present invention have the structure $$\underset{R_2-C=C-CH}{\overset{R_1\ \ R_3\ \ O}{|\ \ \ |\ \ \ \|}}$$

wherein $R_1$ is H or a $C_1$–$C_6$ alkyl radical and $R_2$ and $R_3$ are the same or different and are H or $CH_3$.

These aldehydes thus include acrolein and methacrolein. Where acrolein and/or methacrolein are oxidized, the corresponding alpha-beta-unsaturated carboxylic acid would be acrylic acid and/or methacrylic acid, respectively.

The aldehydes may be oxidized individually or in combinations thereof.

THE REACTION MIXTURE

The components of the reaction mixture which are employed in the process of the present invention, and the relative ratios of the components in such mixtures, are the following 1 mole of aldehyde,
0.2 to 5 moles of molecular oxygen (as pure oxygen or in the form of air),
1 to 25 moles of water (in the form of steam), and
optionally, 0.1 to 5 moles of alpha-beta-unsaturated olefin having the same number of carbon atoms as the aldehyde being oxidized. Propylene, for example, can be used in the reaction mixture when acrolein is being oxidized to acrylic acid.

The water, or steam, can be used as a reaction diluent and as a heat moderator for the reaction. Other diluents which may be used are inert gases such as nitrogen, $CO_2$ and gaseous saturated hydrocarbons.

The olefin may be present due to the fact that the aldehyde feed may be emanating as the effluent from an olefin→aldehyde oxidation reaction process, and such effluent usually contains unreacted olefin.

The components of the reaction mixture are uniformly admixed prior to being introduced into the reaction zone. The components are preheated, individually or after being admixed, prior to their being introduced into the reaction zone, to a temperature of about 200° to 300° C.

REACTION CONDITIONS

The preheated reaction mixture is brought into contact with the catalyst composition, in the reaction zone, under the following conditions:

pressure of about 1 to 10, and preferably of about 1 to 3 atmospheres,
temperature of about 200° to 400° C., and preferably of about 250° to 350° C.,
contact time (reaction mixture on catalyst) of about 0.1 to 10, and preferably of about 1 to 3, seconds, and a space velocity of about 1000 to 6000 $h^{-1}$, preferably 4000 to 5000 $h^{-1}$.

The contact time may also be defined as the ratio between the apparent volume of the catalyst bed and the volume of the gaseous reaction mixture fed to the catalyst bed under the given reaction conditions in a unit of time.

The reaction pressure is initially provided by the feed of gaseous reactants and diluents, and after the reaction is commenced, the pressure is maintained, preferably, by the use of suitable backpressure controllers placed on the gaseous effluent side of the catalyst bed.

The reaction temperature is preferably provided by placing the catalyst bed within a tubular converter whose walls are immersed in a suitable heat transfer medium, such as tetralin, molten salt mixtures, or other suitable heat transfer agent, which is heated to the desired reaction temperature.

The following examples are merely illustrative of the present invention and are not intended as a limitation upon the scope thereof.

The examples provided below disclose the preparation of various catalyst compositions, and the use of such compositions in the oxidation of acrolein to acrylic acid.

The activity of each experimental catalyst was determined in a jacketed one-inch stainless steel reactor or converter tube 78 inches long. The jacket contained tetralin which served as a heat transfer medium.

The center portion (55 inches) of the reactor tube was charged with 800 ml of catalyst with a one-eighth inch movable thermocouple in the catalyst bed.

The catalysts were tested at 30 psig, with a space velocity of 4600 hr$^{-1}$ or contact time of 1.2 seconds, and an inlet feed composed of 3 mole % acrolein, 6 mole % oxygen, 15 mole % steam, and 76 mole % nitrogen.

The activity of the catalysts was tested by adjusting the temperature of the reactor tube jacket to produce a maximum temperature (hot spot) of 304°-306° C. in the catalyst bed, while the oxidation reaction was occurring.

Space velocity is calculated by determining the total reactor outlet gas equivalents (in liters) of the total effluent evolved over a period of one hour. This room temperature volume is converted to the volume at 0° C. at 760 mm Hg.

$$\text{Space Velocity} = \frac{\text{liters of outlet gas equivalents/hour}}{\text{liters of catalyst in reactor}} \qquad \text{IV}$$

$$= \frac{1}{\text{hours at 0° C. and atmospheric pressure}}$$

EXAMPLE 1

$Mo_{2.4}V_{0.6}Ti_{0.3}Fe_{0.15}$ or $Mo_{12.0}V_{3.0}Ti_{1.5}Fe_{0.75}$

Seventy grams of ammonium meta-vanadate (0.6 grams atoms of V) and 424 grams of ammonium paramolybdate (2.4 gram atoms of Mo) were dissolved in two liters of water while stirring at 60°-80° C. in a stainless steel beaker.

To the resulting solution were added 175 grams of titanium ammonium lactate (chelate) solution (containing 0.3 gram atoms Ti) and 60 grams of ferric nitrate [$Fe(NO_3)_3.9H_2O$] (0.15 gram atoms Fe) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 27.2 weight %. Catalytic test results for this material are given in Table I.

EXAMPLE 2

$Mo_{2.4}V_{0.6}Ti_{0.3}Cu_{0.15}$

Seventy grams of ammonium meta-vanadate (0.6 grams atoms of V) and 424 grams of ammonium paramolybdate (2.4 grams atoms of Mo) were dissolved in two liters of water while stirring at 60°-80° C. in a stainless steel beaker.

To the resulting solution were added 175 grams of titanium ammonium lactate (chelate) solution (containing 0.3 gram atoms Ti) and 36 grams of copper nitrate [$Cu(NO_3)_3.3H_2O$] (0.15 gram atoms Cu) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained, is 28.6 weight %. Catalytic test results for this material are given in Table I.

EXAMPLE 3

$Mo_{2.4}V_{0.6}Ti_{0.3}Mn_{0.15}$

Seventy grams of ammonium meta-vanadate (0.6 gram atoms of V) and 424 grams of ammonium paramolybdate (2.4 gram atoms of Mo) were dissolved in two liters of water while stirring at 60°-80° C., in a stainless steel beaker.

To the resulting solution was added 175 grams of titanium ammonium lactate (chelate) solution (containing 0.3 gram atoms Ti) and 54 grams of 50.3% manganese nitrate solution (0.15 gram atoms Mn) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 27.8 weight %. Catalytic test results for this material are given in Table I.

EXAMPLE 4

$Mo_{2.4}V_{0.6}Ti_{0.3}Cr_{0.15}$

Seventy grams of ammonium meta-vanadate (0.6 gram atoms of V) and 424 grams of ammonium paramolybdate (2.4 gram atoms of Mo) were dissolved in two liters of water while stirring at 60°–80° C. in a stainless steel beaker.

To the resulting solution were added 175 grams of titanium ammonium lactate (chelate) solution (containing 0.3 gram atoms Ti) and 60 grams of chromium nitrate $[Cr(NO_3).9H_2O]$ (0.15 gram atoms Cr) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 26.1 weight percent. Catalytic test results for this material are given in Table I.

EXAMPLE 5

$Mo_{2.8}V_{0.7}Ti_{0.35}$

Eighty-two grams of ammonium meta-vanadate (0.7 gram atoms of V) and 494 grams of ammonium paramolybdate (2.8 gram atoms of Mo) were dissolved in two liters of water while stirring at 60°–80° C. in a stainless steel beaker.

To the resulting solution were added 204 grams of titanium ammonium lactate (chelate) solution (containing 0.35 gram atoms Ti) and 28 grams of ammonium nitrate $(NH_4NO_3)$ (0.35 gram moles $NH_4NO_3$) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 30.4 weight %. Catalytic test results for this material are given in Table I.

EXAMPLE 6

$Mo_{2.4}V_{0.6}Ti_{0.3}Cu_{0.15}$ made with $(NH_4OH)_{0.5}$

Seventy grams of ammonium meta-vanadate (0.6 gram atoms of V) and 424 grams of ammonium paramolybdate (2.4 gram atoms of Mo) were dissolved in two liters of water while stirring at 60°–80° C. in a stainless steel beaker.

To the resulting solution were added 175 grams of titanium ammonium lactate (chelate) solution containing 0.3 gram atoms of Ti and 18 grams of ammonium hydroxide containing 28.6% $NH_3$ (0.15 gram moles $NH_3$) plus 36 grams of copper nitrate $[Cu(NO_3)_2.3H_2O]$ (0.15 gram atoms Cu) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 27.8 weight %. Catalytic test results for this material are given in Table I.

EXAMPLE 7

$Mo_{2.4}V_{0.6}Ti_{0.3}Co_{0.15}$

Seventy grams of ammonium meta-vanadate (0.6 gram atoms of V) and 424 grams of ammonium paramolybdate (2.4 gram atoms of Mo) were dissolved in two liters of water while stirring at 60°–80° C. in a stainless steel beaker.

To the resulting solution were added 175 grams of titanium ammonium lactate (chelate) solution (containing 0.3 gram atoms Ti) and 44 grams of cobalt nitrate $[Co(NO_3)_2.6H_2O]$ (0.15 grams atoms Co) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 27.1 weight %.

EXAMPLE 8

$Mo_{2.8}V_{0.7}Ti_{0.175}Cu_{0.175}$

Eighty-two grams of ammonium meta-vanadate (0.7 gram atoms of V) and 495 grams of ammonium paramolybdate (2.8 gram atoms of Mo) were dissolved in two liters of water while stirring at 60°–80° C. in a stainless steel beaker.

To the resulting solution were added 102 grams of titanium ammonium lactate (chelate) solution (containing 0.175 gram atoms Ti) and 42 grams of copper nitrate [Cu(NO$_3$)$_2$.3H$_2$O] (0.175 gram atoms Cu) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 29.2 weight percent. Catalytic test results for this material are given in Table I.

EXAMPLE 9

$Mo_{2.4}V_{0.6}Ti_{0.3}Cu_{0.15}$

Seventy grams of ammonium meta-vanadate (0.6 gram atoms of V) and 424 grams of ammonium paramolybdate (2.4 gram atoms of Mo) were dissolved in two liters of water while stirring at 60°–80° C. in a stainless steel beaker.

To the resulting solution was added a solution containing 84 grams of titanium hydrate pulp (0.3 gram atoms Ti) 54 grams of ammonium lactate (0.6 moles ammonium lactate) and 40 grams 28.6% aqueous ammonium hydroxide (0.67 moles ammonium ion). 36 grams cupric nitrate (0.15 gram atoms Cu) in 100 ml water was then added.

The resulting mixture was heated while stirring and approximately 60 percent of the water was evaporated off.

The resulting concentrated slurry was transferred to a stainless steel evaporating dish and 1040 grams (1000 ml) Norton silica-alumina (#SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 25.8 weight %. Catalytic test results for this material are given in Table I.

EXAMPLE 10

$Mo_{2.4}V_{0.6}Fe_{0.15}$

Seventy grams of ammonium meta-vanadate (0.6 grams atoms of V) and 424 grams of ammonium paramolybdate (2.4 gram atoms of Mo) were dissolved in two liters of water while stirring at 60°–80° C. in a stainless steel beaker.

To the resulting solution were added 60 grams ferric nitrate [Fe(NO$_3$)$_3$.9H$_2$O] (0.15 gram atoms Fe) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 27.5 weight percent. Catalytic test results for this material are given in Table I.

EXAMPLE 11

$Mo_{2.4}V_{0.6}Fe_{0.15}$ made with 0.75 (mole) parts (NH$_4$)$_2$ oxalate

Seventy grams of ammonium meta-vanadate (0.6 gram atoms of V) and 424 grams of ammonium paramolybdate (2.4 gram atoms of Mo) were dissolved in two liters of water while stirring at 60°–80° C. in a stainless steel beaker.

To the resulting solution were added 107 grams of ammonium oxalate [(NH$_4$)$_2$C$_2$O$_4$.H$_2$O] (0.75 gram moles (NH$_4$)$_2$C$_2$O$_4$) and 60 grams of ferric nitrate [Fe(NO$_3$)$_3$.9H$_2$O] (0.15 gram atoms Fe) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (#SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 26.3 weight percent. Catalytic test results for this material are given in Table I.

EXAMPLE 12

$Mo_{2.8}V_{0.7}$

Eighty-two grams of ammonium meta-vanadate (0.7 gram atoms of V) and 256 grams of oxalic acid (2.1 moles) were dissolved in two liters of water while stirring at 60°–80° C. in a stainless steel beaker.

To the resulting solution were added 495 grams of ammonium paramolybdate (2.8 gram atoms Mo) dissolved in 1 liter of water.

The resulting mixture was heated while stirring and approximately 60 percent of the water was evaporated off.

The resulting concentrated slurry was transferred to a stainless steel evaporating dish and 1040 grams (1000 ml) Norton silica-alumina (#SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 26.5 weight %. Catalytic test results for this material are given in Table I.

EXAMPLE 13

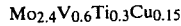
$Mo_{2.4}V_{0.6}Ti_{0.3}Cu_{0.15}$

Seventy grams of ammonium meta-vanadate (0.6 gram atoms of V) and 424 grams of ammonium paramolybdate (2.4 gram atoms of Mo) were dissolved in two liters of water while stirring at 60°-80° C. in a stainless steel beaker.

To the resulting solution were added 84 grams of titanium hydrate pulp (0.3 gram atoms Ti) 39 grams of 28.6% ammonium hydroxide solution (0.67 moles ammonium ion) and 36 grams of cupric nitrate (0.15 gram atoms Cu).

The resulting mixture was heated while stirring and approximately 60 percent of the water was evaporated off.

The resulting concentrated slurry was transferred to a stainless steel evaporating dish and 1040 grams (1000 ml) Norton silica-alumina (#SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 26.0 weight percent. Catalytic test results for this material are given in Table I.

EXAMPLE 14

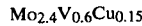
$Mo_{2.4}V_{0.6}Cu_{0.15}$

Seventy grams of ammonium meta-vanadate (0.6 gram atoms of V) and 424 grams of ammonium paramolybdate (2.4 gram atoms of Mo) were dissolved in two liters of water while stirring at 60°-80° C. in a stainless steel beaker.

To the resulting solution were added 90 grams of ammonium lactate solution (containing 0.6 gram nole NH4 lactate) and 36 grams of copper nitrate [Cu(NO3)2.3H2O] (0.15 gram atoms Cu) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 26.0 weight %. Catalytic test results for this material are given in Table I.

The support used in the examples was essentially an (~86/14) $Al_2O_3/SiO_2$ material having an apparent porosity of 36-42% and a surface area of <1 m²/gram. About 100% of the pores in the support had a pore diameter of about 20-180.

The pH of the solutions used in each of the examples for the preparation of the catalysts was in the range of 5±3.

The results of Examples 1 to 8 reported below in Table I demonstrate that when the catalyst compositions are prepared in accordance with the teachings of the present invention, as described above, the resulting catalysts provide a combination of relatively high levels of % conversion, productivity and % selectivity in the oxidation of alpha-beta-unsaturated aldehydes such as acrolein to the corresponding alpha-beta-unsaturated acid.

The results of Examples 9 to 14 reported below in Table I demonstrate that not all compositions containing the elements Mo, V and X, as defined above, provide catalysts which can be used in the oxidation of alpha-beta unsaturated aldehydes such as acrolein to produce the corresponding alpha-beta unsaturated acid at relatively high levels of % conversion, productivity and % selectivity.

TABLE I

| Example | Catalyst Description Atomic Ratios | | Metal* Oxides in Catalyst % | Hot Spot °C. | Conversion, % | AA/Ft³ Cat./ hr. Lbs. | Efficiency % |
|---|---|---|---|---|---|---|---|
| 1  | $Mo_{2.4}V_{0.6}Ti_{0.3}Fe_{0.15}$ |        | 27.2 | 304 | 86.2 | 22.71 | 89.3 |
| 2  | $Mo_{2.4}V_{0.6}Ti_{0.3}Cu_{0.15}$ |        | 28.6 | 305 | 92.4 | 24.62 | 91.2 |
| 3  | $Mo_{2.4}V_{0.6}Ti_{0.3}Mn_{0.15}$ |        | 27.8 | 306 | 90.6 | 22.94 | 89.3 |
| 4  | $Mo_{2.4}V_{0.6}Ti_{0.3}Cr_{0.15}$ |        | 26.1 | 305 | 55.0 | 14.11 | 89.3 |
| 5  | $Mo_{2.8}V_{0.7}Ti_{0.35}$ | (a)    | 30.4 | 304 | 92.3 | 21.35 | 84.2 |
| 6  | $Mo_{2.4}V_{0.6}Ti_{0.3}Cu_{0.15}$ | (b) | 27.8 | 305 | 90.6 | 21.60 | 91.0 |
| 7  | $Mo_{2.4}V_{0.6}Ti_{0.3}Co_{0.15}$ |       | 27.1 | 308 | 90.7 | 21.80 | 87.0 |
| 8  | $Mo_{2.8}V_{0.7}Ti_{0.175}Cu_{0.175}$ |   | 29.2 | 306 | 81.1 | 20.00 | 89.6 |
| 9  | $Mo_{2.4}V_{0.6}Ti_{0.3}Cu_{0.15}$ | (a), (c) | 25.8 | 305 | 52.7 | 11.30 | 81.9 |
| 10 | $Mo_{2.4}V_{0.6}Fe_{0.15}$ |              | 27.5 | 305 | 13.4 | 2.20 | 58.0 |
| 11 | $Mo_{2.4}V_{0.6}Fe_{0.15}$ | (d)         | 26.3 | 318 | 20.3 | 3.10 | 50.9 |
| 12 | $Mo_{2.8}V_{0.7}$ | (a)                  | 26.5 | 305 | 7.7 | 1.40 | 62.9 |
| 13 | $Mo_{2.4}V_{0.6}Ti_{0.3}Cu_{0.15}$ | (c), (f) | 26.0 | 305 | 16.7 | 2.40 | 50.8 |

TABLE I-continued

| Example | Catalyst Description Atomic Ratios | | Metal* Oxides in Catalyst % | Hot Spot °C. | Conversion, % | AA/Ft³ Cat./ hr. Lbs. | Efficiency % |
|---|---|---|---|---|---|---|---|
| 14 | $Mo_{2.4}V_{0.6}Cu_{0.15}$ | (g) | 26.0 | 305 | 30.4 | 7.40 | 83.9 |

AA = acrylic acid
(a) Used 0.35 (mole) parts ammonium nitrate.
(b) Used 0.15 (mole) parts ammonium hydroxide.
(c) Used titanium hydrate pulp.
(d) Used 0.75 (mole) parts ammonium oxalate.
(e) Used 2.1 (mole) parts oxalic acid.
(f) Used 0.67 (mole) parts ammonium hydroxide.
(g) Used 0.60 (mole) parts ammonium hydroxide.
*Oxides of the metals Mo, V, Ti, and/or X.

What is claimed is:

1. A process for the production of unsaturated aliphatic carboxylic acid by vapor phase catalytic oxidation of the corresponding unsaturated aliphatic aldehyde with molecular oxygen in the presence of steam, said aldehyde having the structure $$\underset{R_2-C=C-CH}{\overset{R_1\ \ R_3\ \ O}{|\ \ \ \ |\ \ \ \ \|}}$$

wherein $R_1$ is H or a $C_1$ to $C_6$ alkyl radical and $R_2$ and $R_3$ are the same or different and are H or $CH_3$, which comprises contacting the reaction mixture with a catalytically effective amount of a calcined oxidation catalyst consisting essentially of the elements Mo, V, Ti, and X in the ratio $$Mo_aV_bTi_cX_d$$

wherein X is selected from the group consisting of Fe, Cu, Co, Cr, and/or Mn
 a is 12,
 b is 1 to 14
 c is 0.1 to 12, and
 d is 0.01 to 1.0.

2. A process as in claim 1 in which said unsaturated aliphatic acid is acrylic acid and said unsaturated aliphatic aldehyde is acrolein.

3. A process as in claim 2 in which said oxidation catalyst is supported on an inert support.

4. A process as in claim 3 in which said support is silica, alumina, or silica-alumina.

5. A process as in claim 1 in which a is 12, b is 2 to 8, c is 0.5 to 2 and d is 0.01 to 1.0.

6. A process as in claim 5 in which X comprises Fe.
7. A process as in claim 5 in which X comprises Cu.
8. A process as in claim 5 in which X comprises Co.
9. A process as in claim 5 in which X comprises Cr.
10. A process as in claim 5 in which X comprises Mn.

11. A process for the preparation of an unsaturated aliphatic carboxylic acid by vapor phase catalytic oxidation of the corresponding unsaturated aldehyde having the structure $$\underset{R_2-C=C-CH}{\overset{R_1\ \ R_3\ \ O}{|\ \ \ \ |\ \ \ \ \|}}$$

wherein $R_1$ is H or a $C_1$ to $C_6$ alkyl radical and $R_2$ and $R_3$ are the same or different and are H or $CH_3$, with molecular oxygen in the presence of steam and a solid catalyst at a temperature of between about 220° to 400° C. with a contact time of about 0.1 to 10 seconds, wherein said catalyst consists essentially of the elements Mo, V, Ti and Cr in combination with oxygen and having the empirical formula:

$$Mo_{12}V_bTi_cCr_d$$

wherein
 b is 1 to 14,
 c is 0.1 to 12,
 d is 0.01 to 1.0.

12. A process as in claim 11 in which said unsaturated aliphatic carboxylic acid is acrylic acid and said unsaturated aliphatic aldehyde is acrolein.

13. A process for the production of an unsaturated aliphatic carboxylic acid by the vapor phase catalytic oxidation with molecular oxygen of the corresponding aliphatic aldehyde having the structure:

$$\underset{R_2-C=C-CH}{\overset{R_1\ \ R_3\ \ O}{|\ \ \ \ |\ \ \ \ \|}}$$

wherein $R_1$ is hydrogen or a $C_1$ to $C_6$ alkyl radical and $R_2$ and $R_3$ are the same or different and are H or $CH_3$, which comprises contacting said molecular oxygen and unsaturated aldehyde in the presence of steam with a catalytically effective amount of an oxidation catalyst consisting essentially of the elements Mo, V, Ti, Fe, and Y in combination with oxygen and having the empirical formula:

$$Mo_aV_bTi_cFe_dY_e$$

wherein Y is selected from the group consisting of Co, Cr, and/or Mn,
 a is 12,
 b is 1 to 14,
 c is 0.1 to 12,
 d is a number greater than 0 and up to 3,
 e is 0 to 3 with the proviso that d+e is
3 or less; said catalysts having been prepared by drying an aqueous slurry or solution of salts of said elements followed by calcination.

14. A process as in claim 13 in which said unsaturated aliphatic acid is acrylic acid and said unsaturated aliphatic aldehyde is acrolein.

15. A process as in claim 14 in which said oxidation catalyst is supported on an inert support.

16. A process as in claim 15 in which said support is silica, alumina, or silica-alumina.

17. A process as in claim 16 in which a is 12, b is 2 to 8, c is 0.5 to 2, d is 0.01 to 1.0 and e is 0 to 3 with the proviso that d+e is 3 or less.

18. A process as in claim 13 in which Y comprises Co.
19. A process as in claim 13 in which Y comprises Cr.
20. A process as in claim 13 in which Y comprises Mn.

* * * * *